| United States Patent [19]
Corbière | [11] Patent Number: 4,794,117
[45] Date of Patent: Dec. 27, 1988 |

[54] PROCESS FOR SOLUBILIZING ACTIVE INGREDIENTS AND THE THUS-OBTAINED PHARMACEUTICAL COMPOSITIONS

[76] Inventor: Jérôme Corbière, 17 rue Cortambert, 75016 Paris, France

[21] Appl. No.: 103,451

[22] Filed: Sep. 30, 1987

Related U.S. Application Data

[63] Continuation of Ser. No. 801,148, Nov. 12, 1985, abandoned.

[30] Foreign Application Priority Data

Mar. 3, 1984 [FR] France .................................. 84 1279

[51] Int. Cl.$^4$ ............................................. A61K 31/40
[52] U.S. Cl. .................................................... 514/420
[58] Field of Search ......................................... 514/420

Primary Examiner—Stanley J. Friedman
Attorney, Agent, or Firm—Bierman & Muserlian

[57] ABSTRACT

This invention relates to a novel process for solubilizing the hydrophobic organic compounds—and namely the pharmaceutical active ingredients—in an aqueous phase.

This process is defined in that the hydrophobic compound is prior dissolved in one or several polymers of high molecular weight, then adding to this solution an aqueous medium the pH of which is fixed.

The aqueous solutions thus resulting are useful for preparing medicines for parenteral, digestive, mucous or transcutaneous administration.

6 Claims, No Drawings

PROCESS FOR SOLUBILIZING ACTIVE INGREDIENTS AND THE THUS-OBTAINED PHARMACEUTICAL COMPOSITIONS

PRIOR APPLICATION

This application is a continuation of U.S. patent application Ser. No. 801,148 filed Nov. 12, 1985, now abandoned.

This invention relates to a novel process for making the organic compounds—and namely the pharmaceutical active ingredients—soluble in water or for increasing their solubility in the aqueous media.

The previous studies of Mack (J. Pharm. Sci. 52 (1963) 694 of Swarbrick (J. Pharm. Sci. 54 (1965) 1229) and of N. E. Webb (Bull Parenteral Drug Assoc. 30 (1976) 180), have underlined the significance of the pharamceutical problem due to the use of hydrophobic substances and the difficulties in making them seemingly soluble in water.

The method of solubilizing these authors have employed generally utilizes the formation of micells or the need of mixed solvents in which the active ingredient may be capable of dissolution.

This problem may be queried in a more acute manner when the hydrophobic compounds may not be converted in an ionic form such as a salt of an acid or a salt of a base.

Moreover some derivatives which may be converted into an ionic form are very easily hydrolysed (for ex. salts of a weak base or of an weak acid) or show a pH value which is incompatible with that required for the parenteral administration (very acid solutions or very basic solutions).

Therefore Swarbrick (loc. cit.) has described a general method for dissolving them in an aqueous system which consists in dispersing the active ingredient in the form of micells by means of ionic or non-ionic tensio-active agents. This system however includes two major disadvantages. On one side the active ingredient may be capable of alteration or hydrolysis more quickly than in the system where it is insoluble. On the other side the active ingredient loses a part of its biological activity either by a change in its biological activity or because the micellar particles have an electric charge which alters their binding capacity at the receptor site.

This is the reason why—for example—the phenolic antibacterials lose their activity due to an interaction with the anionic tensioactive agents.

Accordingly if the method of forming micells allows the solubilization in water of some hydrophobic agents, it does not solve the general pharmaceutical problem of administering a soluble compound, the activity, the stability or the penetration in the body of which are kept or even increased in comparison with the insoluble form.

More recently the studies of Webb have shown how difficult was the realization of an injectable aqueous formulation of a water-insoluble compound, Metiapine. The occurrence of crystals in the formulation with propylene glycol/water or ethanol water, the survenue of thrombi provoked by the injection of the solution of the active ingredient in acetic acid made isotonic with mannitol, have made necessary to utilize another medium for making this non-ionizable molecule soluble in water.

This other medium consists in dissolving the active ingredient in an unsaturated fatty acid and emulsifying this lipidic solution in water after addition of a non ionic tensio-active agent. The resulting solution is clear, may have a pH value adjusted within the physiological values and may be sterilized by filtration on a sterilizing filter. This solution causes after the injection the occurrence of haemorragic areas and coloured places. The examination of these areas after necropsy has evidenced some areas of necrosis in the muscular fibers and the formation of granulomas in the giant cells.

The author concluded that the use of this solubilizing medium increased the capacity of irritation due to the active ingredient by virtue of a greater diffusibility of the solution on the site of injection in the presence of a tensio-active agent.

A similar study performed with Terfenadine has shown the necessity to add a marked amount of a non-ionic tensio-active agent to get a clear solution. It has also shown the limits of concentration of the active ingredient in such solutions.

Consequently this dispersing system oil in water does not more allow to solve this technical problem of realizing aqueous pharmaceutical formulations.

Another method for realizing a soluble formulation is that described by J. Gessing and P. J. Toumlin (British J. of Anaesthesia 89 (1977) 954). The active ingredient has been dissolved in a 20% lipidic emulsion (Intralipid). These authors have stated with surprise that with this solution the amounts of active ingredient needed to reach the same state of sedation during medullar anaesthesias have to be twice that needed for an aqueous solution 8.6 mg for a lipidic emulsion 4.92 mg for an aqueous solution The authors have concluded that it happened an interaction with the pharmacokinetics of the active ingredient DIAZEPAM.

Finally it may be judged that the problem of solubilizing active ingredients in an aqueous medium shows two different bearings:

A physico-chemical bearing

The resulting solution has to be stable, at a pH value compatible with the injection or the way of administration and the active ingredient must not be altered by the solubilization A biological bearing The solution has to keep all the pharmacological or chemical activity of the active ingredient and must not modify the characteristics of absorption or the data of pharmacokinetics in an unfavourable way.

The method of solubilizing which is the subject of this invention, brings with it a novel and unexpected answer to a problem set for many years and yet unsolved. It concerns a process using co-solvents whereby the therapeutic compound is dispersed in one or several polymers of ethyleneglycol having a moderate molecular weight without any addition of water, then the resulting pseudo solution is added to an aqueous medium the pH value of which is fixed.

This aqueous medium having a fixed pH value is preferably a buffer solution, the pH value of which is determined as a function of the physico-chemical properties of the molecule of active ingredient.

It may be thought that dispersing the active ingredient in polyethyleneglycol of high molecular weight, causes the formation of micellar particles whereas each molecule of active ingredient is chemically protected by the molecules of polyethyleneglycol and that in this manner the reactive chemical functions of the active ingredient are blocked. The results of this are that the active ingredient is preserved of the effect of any possible hydrolysis or auto-oxydation.

This invention applies more particularly to the problem of solubilizing some molecules which may easily be hydrolyzed or oxidized as for example the N-acyl Indoles such as Indometacine, Cinmetacine, Acemetacine, Nicametacine or Sermetacine. The compounds having a N-acyl function are very easily split and the hydrolysis of this group in neutral or weakly basic medium induces a loss of the activity. This is the situation in most of the steps of salificaton using a strong base thereof.

The invention also extends to the performance of aqueous solutions in which the concentration of active ingredient is high or of aqueous solutions in a small volume.

In a preferred manner of execution, this invention may be defined in that the active ingredient is first dissolved in one or several polymers of ethyleneglycol having a high molecular weight ranging from 300 to 700 as for example polyethyleneglycol 400 or polyethyleneglycol 600 then the aqueous phase the pH value of which is adjusted is added thereto.

The organic phase may further be added with preservative agents, stabilizing agents, flavouring agents, colouring matters, sweetening agents.

In the aqueous phase it may also be added mineral salts, preservating agents, complementary active ingredients which are soluble in water.

Among the preservative agents which are soluble or miscible in the organic phase, it may be cited the Methyl or propyl p. hydroxybenzoates, the isopropyl gallate, or tertbutyl p. hydroxy anisol.

Among the mineral salts which may be added to the aqueous phase it may be cited those needed for making isotonic the aqueous phase such as sodium chloride and lithium chloride.

The mean which determines the pH value is preferably a buffering system as for example the mixture monosodium phosphate-disodium phosphate, the mixture boric acid-sodium borate or the mixture acetic acid-sodium acetate. Administration by the digestive route allows administering solutes the pH of which ranges from 4.5 to 8.0.

Administration by the parenteral route allows administering solutes the pH value of which ranges from 5.5 to 7.5.

Administration through the mucous or transdermal route needs solutes the pH value of which ranges from 5.5 to 7.0.

The selection of a buffering system depends on the compatibility and the efficiency of the route of administration.

The nature of the hydrophobic organic compound to be incorporated into such compositions is very extensive. It may be steroidal compounds such as hormone-like compounds (Estradiol, Estrone, Testosterone, Testosterone propionate, Nor Ethynodiol Acetate, Trenbolone Acetate, Ethynyl Estradiol). It may also be analgetic compounds such as Acetaminophen, Benorylate, Glafenine, Floctafenine, Nicafenine or Anthrafenine. It may also be anti-inflammatory agents such as Piroxicam, Oxicam, Tenoxicam, Ibuprofen, Flurbiprofen, Tiaprofenic acid or Diflunisal.

It may further be uricosuric agents such as Allopurinol, Benzbromarone or Bromarone.

It may be cardio-vascular drugs such as Khelline, Amiodarone, Amrinone, Erythritol pentanitrate.

It may be diuretic agents such as Chlorothiazide, Cyclothiazide, Ethacrynic acid or Triamterene.

It may be antibacterials such as sulfamids, Trimethoprim, semi-synthetic penicillins, esterified or salified Mecrolides such as Erythromycin dipropionate, Josamycin, Phosphonomycin, Tetracyclins, Enniatins, Rifampicins or Cephalosporins.

It may also be hypnotics or anti-epileptic drugs such as Barbiturates, Ureas or Oxazolidones. It may be anti-depressant agents such as Imipramin, Clomipramin, des-methyl Chlorimipramine, Mianserin or Amineptine.

It may be neuroleptic agents such as Haloperidol, Domperidone, Chlorprometazine, Metoclopramide, Sulpiride, Diazepam, Lorazepam, Bromazepam or Nitrazepam.

It may be antifungal agents or anti-trichomonas agents such as Ternidazole, Secnidazole, Miconazole, Econazole or Clotrimazole.

It may further be anti-viral drugs such as Iodo-desoxy Uridine or Citarabine, or anti-mitotic drugs such as Ftorafur or Carmofur.

The percentage of active ingredient in the said compositions ranges from 0.1 to 25 percent and preferably from 1 to 10 percent.

This invention thus provides as a specific subject matter a process for preparing aqueous pharmaceutical compositions intended for the external use as for example auricular, nasal or eye drops characterized in that the active ingredient is dissolved in a polymer of ethylene glycol having a molecular weight ranging from 300 to 700 in which a higher molecular weight polymer of ethylene glycol has optionally been added, then dispersed in an aqueous solution the pH value of which is fixed. The resulting mixture may then be packed in unit dosages or lyophilized in order to be able to be redissolved at the time of use.

The active ingredient may also be dissolved merely in the polymer of ethylene glycol of molecular weight ranging from 300 to 700 and extemporaneously be added to the aqueous buffering system just at the time of use. The aqueous phase may further contain, previously dissolved, another active ingredient which is perfectly soluble in water. This is the point for the eye drops or for the nose drops. It may be convenient to dissolve in the polymer of ethyleneglycol a water insoluble active ingredient as for example an anti-inflammatory agent and to dissolve in the aqueous phase another active ingredient such as a decongestionnant drug as for example Neosynephrin or phenyl propanolamine as the hydrochloride, or an antibacterial such as Chlorhexidin as the gluconate or the sulphate. Mixing the two solutions is extemporaneously performed and allows the simultaneous administration of two active ingredients the action of which is complementary or synergistic.

The following examples illustrate the invention without limiting it.

EXAMPLE I

Eye Drops with Indomethacin

| Solution A | |
|---|---|
| Indomethacin | 0.4 g |
| Methyl p. hydroxybenzoate | 0.2 g |
| Polyethylene glycol 400 | 99.4 g |
| Solution B | |

-continued

| Boric acid | 1.1774 g |
|---|---|
| Sodium chloride | 0.2769 g |
| Sodium Borate | 0.09088 g |
| Water enough for | 100 ml |

The two solutions are prepared and when clear, mixed. The resulting solution is perfectly stable for 4 months at room temperature.

EXAMPLE II

Concentrated Solution of Indomethacin

| Solution A | |
|---|---|
| Indomethacin | 0.0005 g |
| Methyl p. hydroxybenzoate | 0.0025 g |
| Polyethyleneglycol 400 | 3.85 ml |

This solution A is divided in 5 ml flasks at a rate of 1.15 ml per flask.

| Solution B | |
|---|---|
| Boric Acid | 0.04533 g |
| Sodium chloride | 0.01066 g |
| Sodium Borate | 0.0003498 g |
| Water enough for | 3.85 ml |

This solution B is divided in 5 ml-flasks at a rate of 3.85 ml per unit. Solution A kept at 25° C. for 5 months retains 99.8 percent of the amount of active ingredient.

The following table provides the data relating to the conservation tests performed on both solutions of Indomethacin.

EXAMPLE III

Solution of Theophylline

| Solution A | |
|---|---|
| Theophyllin | 4.50 g |
| Propyl p. Hydroxybenzoate | 0.001 g |
| Polyethyleneglycol 600 | 95.5 ml |
| Solution B | |
| Monopotassium phosphate | 0.68 g |
| Di sodium phosphate | 0.71 g |
| Water enough for | 100 ml |

These two solutions are mixed to provide a solution of Theophyllin containing 0.225 g per 10 ml.

EXAMPLE IV

Solution of Hesperidin

| Solution A | |
|---|---|
| Hesperidin | 10 g |
| Isopropyl gallate | 0.002 g |
| Polyethyleneglycol 300 | 90 ml |
| Solution B | |
| Monosodium citrate | 0.20 g |
| Disodium citrate | 0.222 g |
| Aroma Lemon | 0.01 ml |
| Water enough for | 100 ml |

These two solutions are mixed to provide a drinkable solution containing 0.05 g Hesperidin per ml.

TABLE I

Concentration of Indomethacin 0.1 and 0.5%
$T_0$ 0.1% = 0.0997 g % of Indomethacin
$T_0$ 0.5% = 0.498 g % of Indomethacin

| | R (0.1 g %) | | NR (0.5 g %) | |
|---|---|---|---|---|
| | 25° C. | 40° C. | 4° C. | 25° C. |
| 1 month | 0.0988 | 0.0941 | | |
| 2 months | 0.0946 | 0.0866 | | |
| 3 months | 0.0930 | | | |
| 4 months | | | 0.4968 | |
| 5 months | | | | 0.488 |

R = Redissolved
NR = Dissolved
No preservative

What is claimed is:

1. A process for solubilizing indomethacin in water consisting essentially of dissolving an anti-inflammatory amount of indomethacin in a solubilizing amount of at least one polyethylene-glycol having a molecular weight of 300 to 700 and dissolving the resulting solution in a solubilizing amount of an aqueous medium buffered in a pH range of 4.5 to 8.

2. The process of claim 1 wherein the polyethyleneglycol phase may contain at least one member of the group consisting of preservatives, stabilizers, flavoring agents, coloring agents and sweetners.

3. An anti-inflammatory solution produced by the process of claim 1 adapted for oral administration.

4. An anti-inflammatory solution produced by the process of claim 1 adapted for parenteral administration.

5. An anti-inflammatory solution produced by the process of claim 1 adapted for eyedrops administration.

6. A solution of claim 3 wherein amount of indomethacin is 0.1 to 1.0%.

* * * * *